(12) United States Patent
Gardiner et al.

(10) Patent No.: US 6,602,905 B1
(45) Date of Patent: Aug. 5, 2003

(54) N-ACYL HOMOSERINE LACTONES FOR THE TREATMENT OF CARDIAC TACHYARRHYTHMIAS, ISCHAEMIC HEART DISEASE OR CONGESTIVE HEART FAILURE

(75) Inventors: Sheila Margaret Gardiner, Nottingham (GB); Terence Bennett, Nottingham (GB); Barrie Walsham Bycroft, Nottingham (GB); David Idris Pritchard, Leics (GB); Paul Williams, Nottingham (GB)

(73) Assignee: The University of Nottingham, Nottingham (GB)

( * ) Notice: Subject to any disclaimer, the term of this patent is extended or adjusted under 35 U.S.C. 154(b) by 0 days.

(21) Appl. No.: 10/110,465
(22) PCT Filed: Oct. 6, 2000
(86) PCT No.: PCT/GB00/03830
§ 371 (c)(1),
(2), (4) Date: Aug. 21, 2002
(87) PCT Pub. No.: WO01/26650
PCT Pub. Date: Apr. 19, 2001

(30) Foreign Application Priority Data

Oct. 13, 1999 (GB) .............................................. 9924195

(51) Int. Cl.⁷ .............................................. A01K 31/34
(52) U.S. Cl. ..................................................... 514/472
(58) Field of Search .......................... 514/472; 549/321

(56) References Cited

FOREIGN PATENT DOCUMENTS

| EP | 0 925 786 A | 6/1999 |
|---|---|---|
| WO | WO 92 18614 A | 10/1992 |
| WO | WO 95 01175 A | 1/1995 |
| WO | WO 96 40746 A | 12/1996 |

OTHER PUBLICATIONS

Robson N.D.: "Bacterial N–Acyl–Homoserine–Lactone–Dependent Signalling and Its Potential Biotechnological Applications"; *TIBTECH*, vol. 15, 1997, pp. 458–464;.
Zhu Jun et al.: "Analogs of the Autoinducer 3–Oxooctanoyl– Homoserine Lactone Strongly Inhibit Activity of the TraR Protein of Agrobacterium Tumefaciens"; *Journal of Bacteriology*, vol. 180. No. 20, Oct. 1998, pp. 5398–5405.
Parsek M. et al.: "Acyl Homoserine–Lactone Quorum–Sensing Signal Generation"; *Proceedings of the National Academy of Sciences of USA*, National Academy of Science. Washington, US, vol. 96, Apr. 1999, pp. 4360–4365.
Lawrence R. N. et al.: "The Pseudomonas Aeruginosa Quorum–Sensing Signal Molecule, N–(3–oxododecanoyl)–L–Homoserine Lactone, Inhibits Porcine Arterial Smooth Muscle Contraction"; *British Journal of Pharmacology*, vol. 128, No. 4, Oct. 1999, pp. 845–848.
Gardiner, S. M. (1) et al.: "N–(3–oxododecanyl)–L–Homoserine Lactone Causes Bradycadia in Conscious Rats"; *British Journal of Pharmacology*, Jan. 2000, vol. 129, No. Proceedings Supplements, pp. 47P. Print. Meeting Info.: Meeting of the British Pharmacology Society Cambridge, England, UK Jan. 05–07, 2000 British Pharmacological Society.

*Primary Examiner*—Amelia A. Owens
(74) *Attorney, Agent, or Firm*—Bret E. Field; Bozicevic, Field & Francis

(57) ABSTRACT

Compounds having anti-fibrotic effects are provided. Also provided is a method for treating disorders, diseases or conditions associated with pathological fibrotic states. The compounds useful in the present invention are homocysteine thiolactone and selected derivatives thereof.

8 Claims, 3 Drawing Sheets

Figure 1:
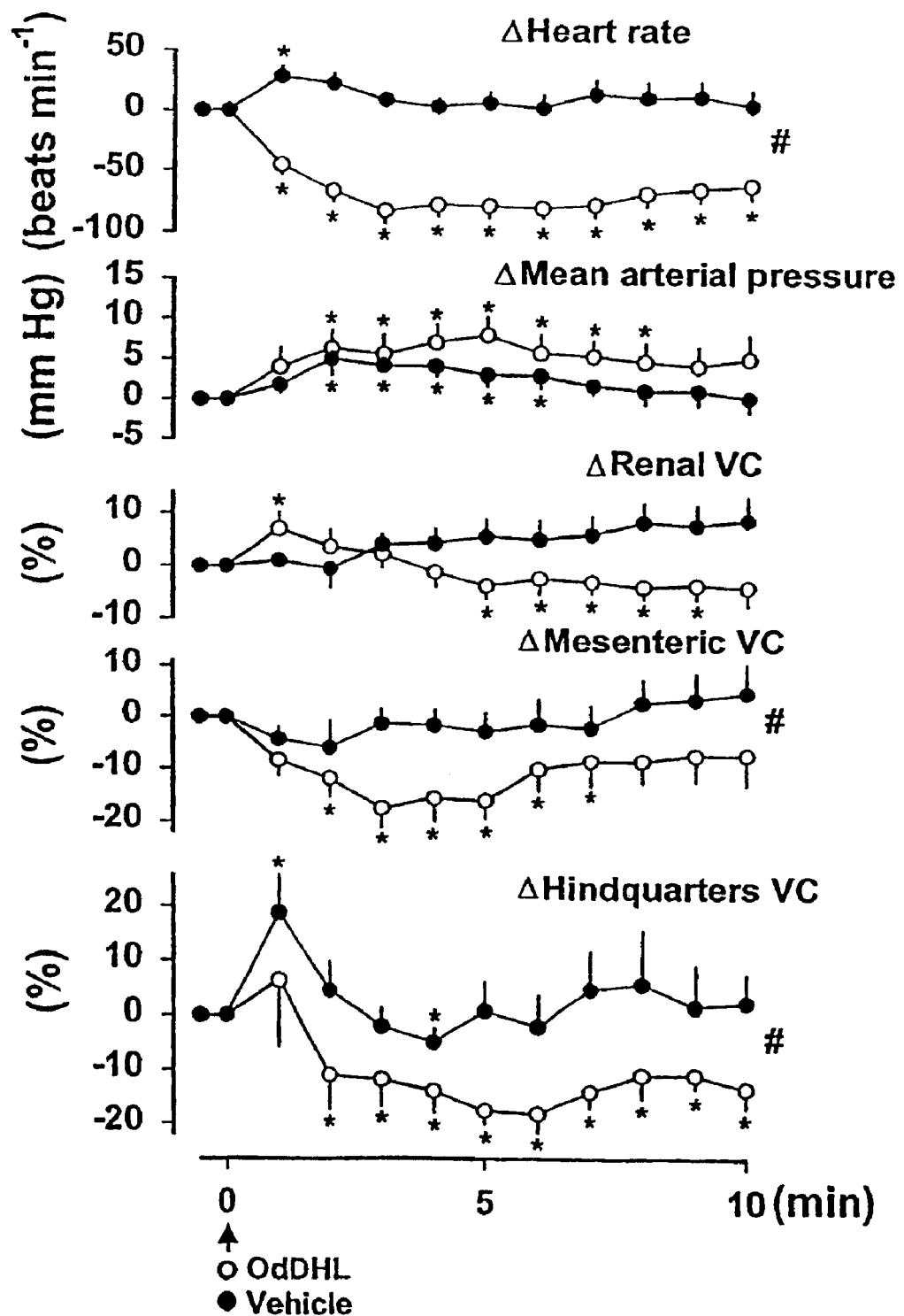

N-ACYL HOMOSERINE LACTONES FOR THE TREATMENT OF CARDIAC TACHYARRHYTHMIAS, ISCHAEMIC HEART DISEASE OR CONGESTIVE HEART FAILURE

This invention relates to certain N-acyl homoserine lactones which have use in the treatment or prevention of cardiac tachyarrhythmias, ischaemic heart disease or congestive heart failure. It, further, relates to a method for the treatment or prevention of tachyarrhythmias, ischaemic heart disease or congestive heart failure and to compositions used in the method.

Many anti-arrhythmic agents and compounds for the treatment of ischaemic heart disease or congestive heart failure that are currently used clinically have several unwanted side effects. One such side effect is hypotension. It is a major disadvantage that in slowing down the heart beat, an anti-arrhythmic drug also, for example, reduces the average blood pressure. The present invention is based on the discovery by the inventors that certain N-acyl homoserine lactone compounds can reduce the heart beat without substantially reducing arterial blood pressure.

Previously, certain N-acyl homoserine lactones (AHL) have been shown to exhibit immunosuppressant activity and to inhibit the release of histamine. For instance, WO 95/01175 discloses that compounds having the following formula (A):

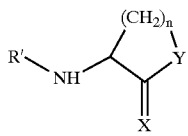

wherein n is 2 or 3; Y is O, S or NH; X is O, S or NH; and $R^1$ is $C_1$–$C_{18}$ alkyl or acyl which may be substituted have use in the treatment of allergic diseases, such as asthma, hayfever and autoimmune diseases. There is, however, no teaching or suggestion in this document that a defined subgroup of AHL compounds has any activity that could make such compounds useful in the management of tachyarrythmias, ischaemic heart disease or congestive heart failure.

Accordingly, the invention provides a method for the treatment or prevention of cardiac tachyarrhythmias, ischaemic heart disease and congestive heart failure in human and non-human mammals, which method comprises the administration of an effective, non-toxic amount of a compound of the formula (I):

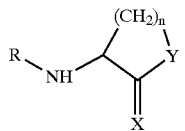

wherein n is 2 or 3; Y is O, S or NH; X is O, S or NH; and R is 3–15C substituted aliphatic acyl group.

In a further aspect, the present invention provides the use of a compound of formula (I) above for the manufacture of a medicament for the treatment or prevention of cardiac tachyarrhythmias, ischaemic heart disease and congestive heart failure.

The group R, in formula I above, is a substituted aliphatic acyl group which, in total, has from 3 to 15 carbon atoms. By "acyl group" we mean a group which has a terminal carbonyl which is attached directly to the nitrogen atom which itself is attached to the lactone ring. By the term "substituted" we mean that the aliphatic acyl group is substituted in or on the carbon chain of the aliphatic group. Preferably, R is a substituted alkyl carbonyl group wherein the substituted alkyl has from 2 to 14 carbon atoms and is substituted at position β to the carbonyl and, optionally, elsewhere. Preferred substituents at the β or 3-position are oxo and hydroxy, with the 3-oxo substituent group being more preferred.

The alkyl of the substituted alkylcarbonyl group for R in formula I may be a straight chain group or a branched chain group, either of which may be substituted internally in the carbon chain or on the carbon chain with a heteroatom, e.g., O, S, NH or $NR^1$, where $R^1$ is a hydrocarbyl group. Preferred are straight chain groups in order to minimise the lipophilic nature of the compound. If the alkyl group is branched then preferably it will have secondary branching only at or near to the end of the group remote from the carbonyl group. Although the chain length of such a substituted alkylcarbonyl group may range broadly from 3 to 15 carbon atoms, groups at the higher end of this carbon content range are preferred, i.e., the substituted alkyl group itself preferably contains from 9 to 14 carbon atoms and is more preferably a 11 to 13C group and most preferably an 11 or 1 2C group. Particular examples of an N-acyl group in formula I, thus, include 3-oxododecanoyl and 3-oxoundecanoyl. The compound N-3-oxoundecanoyl-L-homoserine lactone is, we believe, a novel compound and, as such, forms a further aspect of the present invention as do pharmaceutical compositions containing it together with a pharmaceutically acceptable carrier or diluent.

It is preferred, in the present invention, that n is 2 and both Y and X are oxygen. It should be noted that the compounds having the formula I above possess a chiral centre in the ring carbon atom attached to the RNH-group. The present invention relates to the use of both L-and D-isomers separately, as well as to the use of racemic mixtures.

The compounds of the formula I have been found to reduce substantially the heart rate in normal rats with little or no effect on the mean arterial pressure. A reduction from a normal heart rate in a rat of about 350 beats per minute by as much as 100 beats per minute has been shown by the inventors. The compounds of the formula I therefore have potential as agents for treating tachyarrhythmias, ischaemic heart disease and congestive heart failure in humans. Obviously, an amount effective to treat tachyarrhythmia, ischaemic heart disease and congestive heart failure hereinbefore described will depend upon several factors such as the efficacy of the active compound used, the nature and severity of the disorder being treated, the age and body weight of the patient being treated and the nature of any concurrent treatment, if any. A typical dose of the active compound is, in most cases, less than 10 mg per kg of body weight of the patient. Pharmaceutical compositions containing the active compound described herein may be administered in a number of ways as will be apparent to one of ordinary skill. Administration may, typically, be by parenteral route or by a formulation to be taken orally. The active compound when it is to be administered by a parenteral route will preferably be administered by intravenous injection or intravenous infusion. Thus, for such administration, fluid unit dose forms are prepared. containing a compound of the formula I and a sterile vehicle. The dose form will normally be prepared by dissolving the active compound in the vehicle, for example acetonitrile/dextrose or, preferably, a sterile saline solution and subjecting the solution to sterilisation before being filled into a suitable vial or ampoule and then sealing. It may further be advantageous to incorporate, into the vehicle, various additives such as a local anaesthetic, preservatives, buffer, stabilizer or pH adjuster. In the case of chronic treatment of tachyarrhythmias, however, the active compound will preferably be administered as an oral formulation, typically in the form of tablets, pills or capsules. Such formulations may include other suitable additives which are known in the art, such as binders, diluents and flavouring agents.

EXAMPLES

1. Synthesis of N-(3-Oxoalkanoyl)-L-homoserine Lactones

Triethylamine (1 mmol) was added to a stirred solution of homoserine lactone hydrochloride (the L-or D-isomer or a racemic mixture) (1 mmol) in water (2 ml) followed by the addition of ethylene glycol ketal of 3-oxoalkanoic acid (1 mmol) and 1-ethyl-3-(3-dimethylaminopropyl) carbodiimide hydrochloride (1 mmol). The mixture was stirred for 20 h and then rotary evaporated to dryness at about 35° C. The light orange residue was extracted with warm ethyl acetate (5×5 ml), and the extracts pooled and washed successively with water (1×3 ml), 5% sodium bicarbonate solution (1×3 ml) and finally brine (1×5 ml). Drying ($MgSO_4$) and evaporation of solvent in vacuo gave the ethylene alycol ketal of 3-oxoalkanoylated homoserine lactones (40–50%).

Perchloric acid (60%, 0.25 ml) was added to an ice-cooled solution of the alkanoylated lactone (0.5 mmol) in dichloromethane (15 ml). The mixture was stirred at 0° C. for 0.5 h and then at room temperature for 1.5 h. The solvent was removed in vacuo and the residue re-dissolved in ethyl acetate (20 ml). The solution was washed with cold water (2×5 ml) and brine (1×5 ml), dried ($MgSO_4$) and rotary evaporated to obtain the desired N-(3-oxoalkanoyl) homoserine lactones (55–60%).

2. Synthesis of N-Acylated Homoserine Lactone

Triethylamine (1 mmol) was added to a stirred solution of homoserine lactone hydrochloride (the L-or D-isomer or a racemic mixture) (1 mmol) in water (2 ml) followed either by the addition of acid anhydride (3 mmol) or acid (1.5 mmol) and 1-ethyl-3-(3-dimethylaminopropyl) carbodiimide hydrochloride (1.5 mmol). The mixture was stirred at room temperature overnight and then evaporated in vacuo to dryness. The residue was partitioned between water (5 ml) and ethyl acetate (20 ml) and the organic layer successively washed with 5% $NaHCO_3$ solution (2×5 ml), 1 M $KHSO_4$ solution (1×5 ml) and brine (1×5 ml). Drying ($MgSO_4$) and removal of solvent gave the title acylated lactones (20–60%).

3. Synthesis of N-(3-Hydroxyalkanoyl)-L-homoserine Lactones

N-(3-Oxoalkanoyl)-L-homoserine lactone (0.2 mmol) was dissolved in methanol (5 ml) and the solution made acidic (pH 3–4) with 2 M HCl-methanol. Sodium cyanoborohydride (0.5 mmol) was added in one lot with stirring and the reaction mixture maintained at pH 3–4 by the occasional addition of 2 M HCl-methanol. After 2h, solvent was removed in vacuo and ethyl acetate extracts (3×5 ml) of the residue were combined, dried ($MgSO_4$) and evaporated to yield the title hydroxy derivatives. The products were purified by preparative layer chromatography on silica plates in $CHCl_3$-MeOH (9:1) and repurified by HPLC. The latter may be resolved and the diastereoisomers separated.

The compounds prepared by these methods were more than 90% pure and were further purified with reverse phase HPLC using a 1×25 cm S50DS2 semi-prep column eluting isocratically with 15–20% $MeOH-H_2O$ mixture and monitoring at 210 nm. The products were freeze-dried and stored below 0° C.

4. Synthesis of N-(3-Oxoundecanoyl)-L-homoserine Lactone

To a stirred solution of nonanoic acid (1 mmol) in dry dichloromethane (30 ml) was added 4-dimethylaminopyridine (1.05 mmol) and 1,3-dicyclohexylcarbodiimide (1.05 mmol). After 1h Meldrum's acid (1 mmol) was added and the mixture stirred at room temperature overnight. The mixture was filtered to remove dicyclohexylurea and then evaporated to dryness. The residue was taken up in ethyl acetate and washed with 2M hydrochloric acid (2×20 ml) and the organic layer dried ($MgSO_4$). Rotary evaporation afforded the crude intermediate product, nonanoyl Meldrum's acid, in 93% yield.

To a stirred solution of nonanoyl Meldrum's acid (1.5 mmol) in acetonitrile (30 ml) was added L-homoserine lactone hydrochloride salt (1 mmol) and triethylamine (1.2 mmol). The mixture was stirred at room temperature overnight and then refluxed for 3h. The mixture was evaporated to dryness. The residue was taken up in ethyl acetate and washed with sodium hydrogen carbonate (20 ml), potassium hydrogen sulphate (20 ml), brine (20 ml) and dried ($MgSO_4$). The solution was rotary evaporated to yield the crude product which was purified by chromatography on silica plates in ethyl acetate (Rf 0.5) to obtain pure N-(3-oxoundecanoyl)-L-homoserine lactone in 74% yield.

$^1$H NMR(250 MHz, $CDCl_3$)δ0.88(3H,t,$CH_3$), 1.27(10H, s,$CH_3(CH_2)_5$), 1.60(2h,m,$CH_2CH_2CO$), 2.29(1 H,m,4α-H), 2.55(2H,t,$CH_2CO$), 2.69(1 H,m,4β-H), 3.48(2H,s, $COCH_2CO$), 4.28(1H,m,5α-H), 4.43(1 H,td,5β-H), 4.63(1 H,m,3-H), 7.77(1 H,d,NH). ES-MS m/z 284(M+H, $C_{15}H_{25}NO_4$ requires m/z 283).

EXPERIMENTAL METHODS

Male rats (Long Evans) of body mass in the range of from 350 to 450 g were used in the experiments.

The rats were instrumented with probes to monitor blood flow in renal, mesenteric and hindquarters vascular beds and with catheters to measure blood pressure and heart rate and to administer substances intravenously.

Measurements of the cardiovascular variables were made in the test rats which were conscious and able to move freely during the duration of the test procedure (10 minutes). The raw data were sampled (every 2 ms), averages were calculated (per cardiac cycle) and the data was stored to diskette (every 5 s). The stored data was analysed off line.

1. Experiment I

The following substances were administered by intravenous injection to the test rats.

1) vehicle only (100 μl of 50:50 acetonitrile:dextrose)
2) 10 mg per kg body weight of N-(3-oxododecanoyl) homoserine lactone (OdDHL; Formula I; n=2, Y=X=O, R=3-oxododecanoyl). The OdDHL was dissolved in acetonitrile/dextrose (50 μl:50 μl) 100 μl.

The cardiovascular profile is shown in FIG. 1. This figure shows the effect of the introduced vehicle (●) and the effect of the introduced OdDHL (○) on the heart rate of the rats (top), on the mean arterial pressure (second from top), on the renal vascular conductance (third from top), on the mesenteric vascular conductance (second from bottom) and on the hindquarters vascular conductance (bottom).

It can be seen, from FIG. 1, that OdDHL caused profound bradycardia. However, substantially no change in the mean arterial blood pressure was observed. It was, also, noted that blood flow, particularly in the mesenteric and hindquarters, was reduced in animals tested with OdDHL.

2. ExDeriment II

The following substances were administered intravenously to the test rats.

1) As in 2) in Experiment I above (○)
2) Atenolol +atropine then as in 2) in Experiment I above (●).

Figure 2:
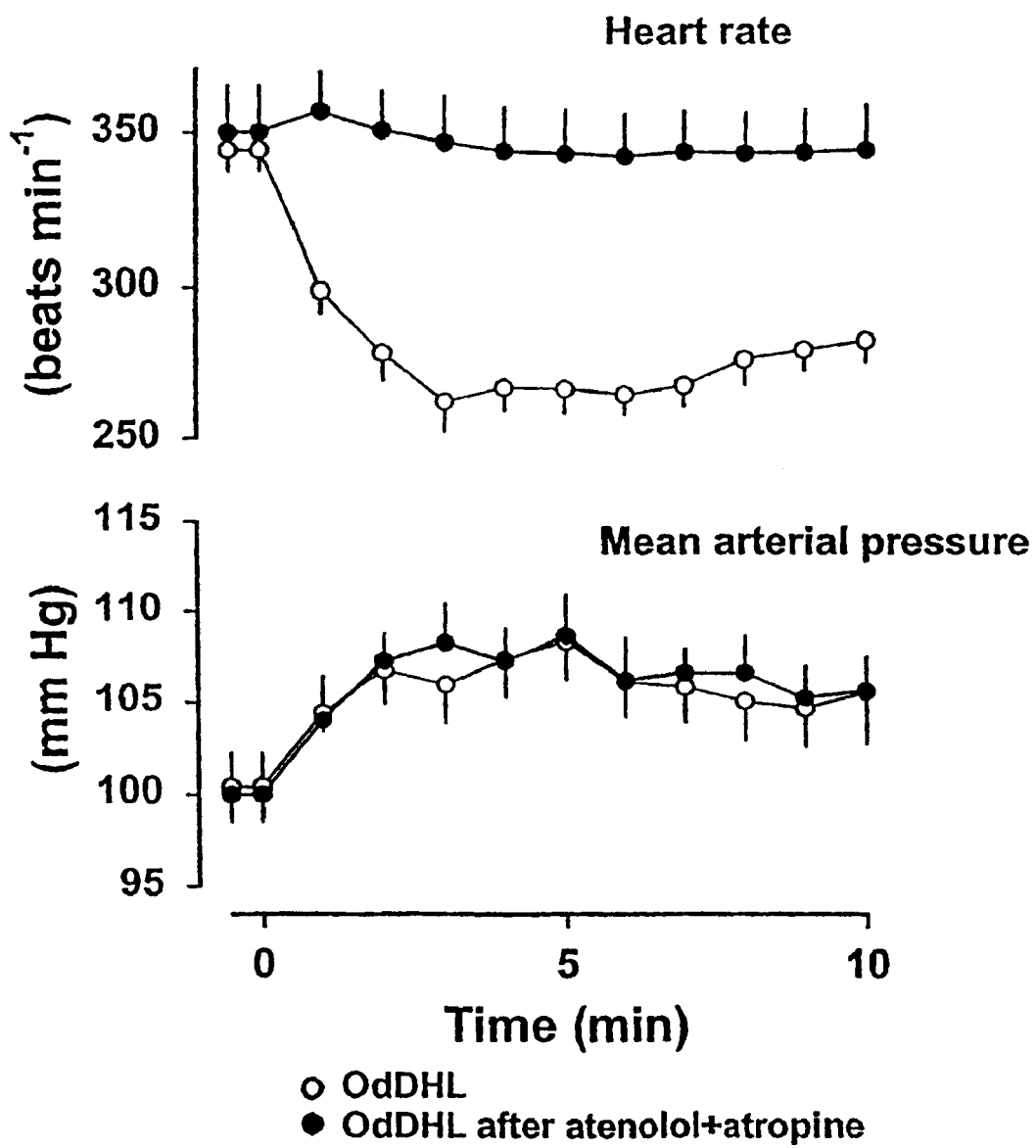

The cardiovascular profile is shown in FIG. 2. This figure shows the effect on the heart rate of OdDHL and of OdDHL after atenolol-atropine (top) and the effect on the mean arterial blood pressure.

It can be seen, from FIG. 2, that the bradycardia induced by OdDHL administered on its own was not observed after cardiac autonomic blockade was induced by an earlier administration of atenolol and atropine, thus indicating that the effects of the OdDHL were largely indirect such that it can be concluded that the OdDHL was not acting directly on the pacemaker of the heart to slow down the heart rate.

3. ExDeriment III

The following substances were administered by intravenous injection to the test rats.

3) vehicle only (100 µl of 50:50 acetonitrile:dextrose)
4) 10 mg per kg body weight of N-(3-oxoundecanoyl) homoserine lactone (OuDHL; Formula I; n=2, Y=X=O, R=3-oxoundecanoyl).

The OuDHL was dissolved in acetonitrile/dextrose (50 µl:50 µl) 100 µl.

Figure 3:
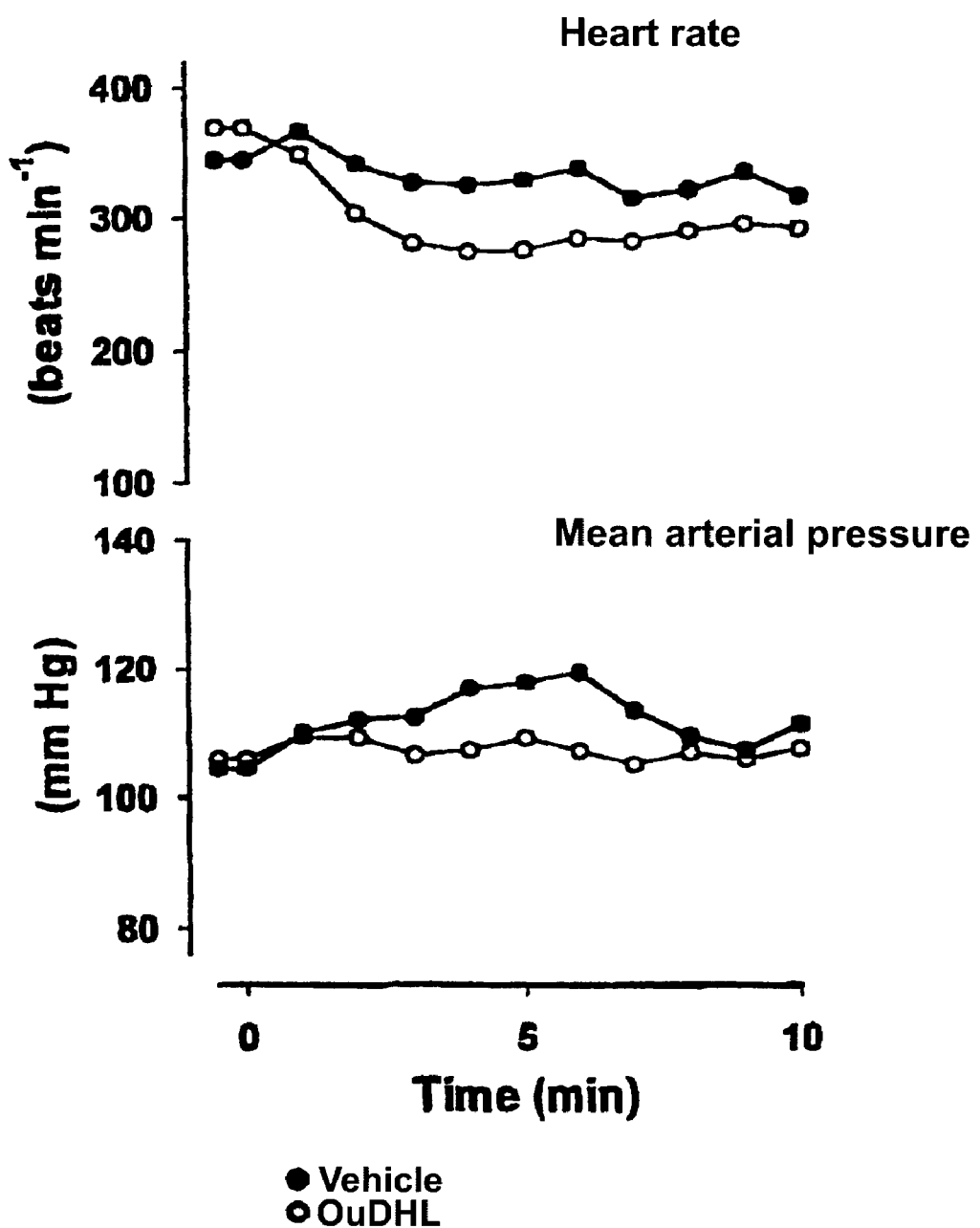

The cardiovascular profile is shown in FIG. 3. This figure shows the effect of the introduced vehicle (●) and the effect of the introduced OuDHL (○) on the heart rate of the rats (top) and on the mean arterial pressure (bottom).

It can be seen, from FIG. 3, that OuDHL caused marked bradycardia. However, substantially no change in the mean arterial blood pressure was observed.

What is claimed is:

1. A method for the treatment or prevention of cardiac tachyarrythmias, ischaemic heart disease or congestive heart failure in human and non-human mammals comprising administering an effective, non-toxic amount of a compound of the formula I:

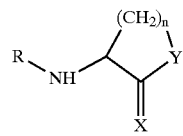

wherein n is 2 or 3; Y is O or NH; X is O or NH; and R is a 3–15C substituted aliphatic acyl group.

2. A method according to claim 1, wherein R is a substituted aikylcarbonyl group in which the substituted alkyl has from 2 to 14 carbon atoms and is substituted at position β to the carbonyl and, optionally, elsewhere.

3. A method according to claim 2, wherein the substituted alkyl has from 9 to 14 carbon atoms.

4. A method according to claim 3, wherein the substituted alkyl has from 11 to 13 carbon atoms.

5. A method according to claim 4, wherein the substituted alkyl has 11 or 12 carbon atoms.

6. A method according to claim 2, wherein the substituted alkyl is substituted at position β to the carbonyl group by an oxo group or an hydroxy group.

7. A method according to claim 6, wherein n is 2, Y is O, X is O and R is a 3-oxododecanoyl group.

8. A method according to claim 6, wherein n is 2, Y is O, X is O and R is a 3-oxoundecanoyl group.

* * * * *